US010323263B2

(12) United States Patent
Johansson et al.

(10) Patent No.: US 10,323,263 B2
(45) Date of Patent: Jun. 18, 2019

(54) METHODS FOR PRODUCING LIQUID COMPOSITIONS COMPRISING β-GLUCAN

(71) Applicant: Tate & Lyle Sweden AB, Kimstad (SE)

(72) Inventors: Ingbritt Johansson, Kimstad (SE); Mark Lawther, Kimstad (SE); Bart Moyson, Kimstad (SE); Ola Anderson, Kimstad (SE)

(73) Assignee: Tate & Lyle Sweden AB, Kimstad (SE)

( * ) Notice: Subject to any disclaimer, the term of this patent is extended or adjusted under 35 U.S.C. 154(b) by 0 days.

(21) Appl. No.: 15/666,468

(22) Filed: Aug. 1, 2017

(65) Prior Publication Data
US 2017/0349924 A1 Dec. 7, 2017

Related U.S. Application Data

(63) Continuation of application No. PCT/EP2016/052201, filed on Feb. 2, 2016.

(30) Foreign Application Priority Data

Feb. 3, 2015 (GB) .................................. 1501799.9
Nov. 2, 2015 (GB) .................................. 1519344.4

(51) Int. Cl.
C12P 19/14 (2006.01)
C12P 19/04 (2006.01)
C12P 19/02 (2006.01)
C08B 37/00 (2006.01)
C08H 8/00 (2010.01)
B02C 9/04 (2006.01)

(52) U.S. Cl.
CPC ............... *C12P 19/14* (2013.01); *B02C 9/04* (2013.01); *C08B 37/0024* (2013.01); *C08H 8/00* (2013.01); *C12P 19/02* (2013.01); *C12P 19/04* (2013.01); *C12Y 302/01* (2013.01)

(58) Field of Classification Search
None
See application file for complete search history.

(56) References Cited

U.S. PATENT DOCUMENTS

2003/0153746 A1   8/2003  Van Lengerich et al.
2005/0153044 A1   7/2005  Hellweg et al.

FOREIGN PATENT DOCUMENTS

| CA | 2421637 A1 | 4/2002 |
| CN | 102108372 * | 6/2013 |
| CN | 103750258 A | 4/2014 |
| WO | 0024270 A1 | 5/2000 |
| WO | 0049052 A2 | 8/2000 |
| WO | 121012 A1 | 3/2001 |
| WO | 126479 A1 | 4/2001 |
| WO | 02051873 A1 | 7/2002 |
| WO | 2004085484 A1 | 10/2004 |
| WO | 2004096862 A2 | 11/2004 |
| WO | 2004099428 A1 | 11/2004 |
| WO | 2005048735 A1 | 6/2005 |
| WO | WO2005048735 * | 6/2005 |
| WO | 2008151439 A1 | 12/2008 |
| WO | 2009038938 A1 | 3/2009 |
| WO | 2010000935 A1 | 1/2010 |
| WO | 2016124608 A1 | 8/2016 |

OTHER PUBLICATIONS

Aman et al. Journal of Cereal Science (1985), 3(3), 231-7.*
Hua et al. PLoS One. Nov. 21, 2014;9(11), pp. 1-17.*
Knuckles B E et al: "Beta-Glucan-Enriched Fractions From Laboratory-Scale Dry Milling and Sieving of Barley and Oats", Cereal Chemistry, AACC International Inc, US, vol. 69, No. 2, Jan. 1, 1992 (Jan. 1, 1992 ), pp. 198-202.
Wang et al: "Dry processing of oats—1-29 Application of dry milling", Journal of Food Engineering, Barking, Essex, GB, vol. 82, No. 4, May 14, 2007 (May 14, 2007), pp. 559-567, XP022077930, ISSN: 0260-8774, DOI: 10.1016/J.JFOODENG.2007.03.011 figure 7; table 2.
GB Search Report dated Apr. 18, 2016 for GB Application No. GB1519344.4.
GB Search Report dated Aug. 4, 2015 for GB Application No. GB1501799.9.
PCT Search Report and Written Opinion dated Apr. 29, 2016 for PCT Application No. PCT/EP2016/052201.

* cited by examiner

*Primary Examiner* — Christian L Fronda
(74) *Attorney, Agent, or Firm* — EIP US LLP

(57) ABSTRACT

The present invention relates to methods of processing mixtures comprising β-glucans and polysaccharides.

20 Claims, 6 Drawing Sheets

METHODS FOR PRODUCING LIQUID COMPOSITIONS COMPRISING β-GLUCAN

CROSS-REFERENCE TO RELATED APPLICATIONS

This application is a continuation of International Application No. PCT/EP2016/052201, filed Feb. 2, 2016, which claims the benefit of GB Application No. GB1501799.9, filed Feb. 3, 2015, and GB Application No. GB1519344.4, filed Nov. 2, 2015. Each of the above-referenced patent applications is hereby incorporated by reference in its entirety.

BACKGROUND OF THE INVENTION

Technical Field

The present invention relates to methods of processing mixtures comprising β-glucans and polysaccharides.

Background

β-glucans are polysaccharides of D-glucose monomers linked by β-glycosidic bonds, which occur naturally in some yeast, fungi, plants and bacteria. β-glucans occur in various forms, such as (1,3)-β-glucan, (1,4)-β-glucan, (1,6)-β-glucan, (1,3;1,6)-β-glucan and (1,3;1,4)-β-glucan. The designations (1,3), (1,4) and (1,6) refer to the type of bond found in the β-glucan, and designate the carbon atoms in the D-glucose monomers between which the β-glycosidic bond is formed. Some, but not all, β-glucans are water-soluble. (1,3;1,4)-β-glucans are generally water soluble, at least at sizes below 2,000,000 Daltons. β-glucans are notably found in cereal grains, for example, wheat, barley, rye, and oat. Oats are a particularly good source of (1,3;1,4)-β-glucan.

Liquid compositions comprising β-glucans have been shown to be useful in a variety of ways, including as a food additive, a nutritional supplement, in pharmaceutical compositions, in healthcare, for hair care, skin care and for use in cosmetics. Particularly with regard to skin care, compositions comprising β-glucan have been shown to reduce erythema, as well as acting as an anti-irritant, and can be used to provide relief from insect bites. β-glucan compositions can also be applied to sooth the skin, providing relief from sunburn. β-glucan compositions are also used as an emollient.

Within oat, β-glucans are found predominantly in the aleurone layer and sub-aleurone layers of the grain. In conventional methods for processing grain, the aleurone layer is generally removed with the bran, whilst the sub-aleurone layers are retained as part of the endosperm. Consequently, conventional methods of processing grain are not suitable for maximising the recovery of β-glucans from oats.

In order to produce a β-glucan composition which is suitable for use in cosmetics and health care, it is desirable to produce a composition which comprises β-glucan without significant contamination with other undesirable components of the grain. Several processes have been tried to achieve this. For example, WO 2004/096862 discloses a method to extract and purify cereal β-glucans from milled bran via the use of alkaline extraction and alcohol precipitation. However, this process suffers from being expensive. Further, consumers increasingly wish to purchase naturally produced products. In many countries, in order for a product to be labelled as natural, certain legal and/or regulatory requirements must be met. These often prescribe processes which may not be used in relation to the production of "natural" products. Alkaline extraction and alcohol precipitation are often cited as proscribed forms of processing for natural products, meaning that where alkaline extraction or alcohol precipitation is used to extract β-glucans from cereal grains, in many countries the resultant β-glucan may not be labelled as "natural". This means the resultant product is less commercially attractive.

A further problem with extraction methods based on alkaline or alcohol extraction is that there are often residual impurities which result in a β-glucan composition which is prone to hazing. Compositions prone to hazing are undesirable, and potentially unsuitable for a variety of uses, particularly for consumer products such as cosmetics and food. US2014/0066510 discloses a method of producing oat extracts which addresses this, but results in a composition with almost no β-glucan.

Different uses of β-glucan compositions may require or benefit from the provision of β-glucans having an average size in a particular range. A further drawback of the processes referred to above is that these processes do not provide the ability to control the size of the β-glucans in the resultant composition.

Therefore there remains a need for a cost effective means of producing liquid compositions comprising β-glucan suitable for a range of uses.

SUMMARY

According to a first aspect of the present invention, there is provided a method of processing a mixture comprising β-glucan, polysaccharides and no more than 5% w/w of oil and no more than 1% w/w of protein, wherein the method comprises: subjecting the mixture to at least one enzymatic treatment, the enzymatic treatment degrading at least a portion of the polysaccharides; and filtering the enzymatically treated mixture. In some embodiments, the means of filtration is membrane filtration. In some embodiments, a filter with pores of between 0.45-1.5 μm, and optionally 0.8-1.0 μm, may be used.

In one embodiment the method comprises processing a mixture comprising β-glucan, polysaccharides and no more than 4% w/w of oil and no more than 1% w/w of protein.

In one embodiment the method comprises processing a mixture comprising β-glucan, polysaccharides and no more than 2% w/w of oil and no more than 1% w/w of protein.

In one embodiment the method comprises processing a mixture comprising β-glucan, polysaccharides and no more than 1% w/w of oil and no more than 1% w/w of protein.

In one embodiment, prior to enzymatic treatment and filtration the β-glucan is present in the mixture at an amount of about 1.5% w/w.

In one embodiment, the method comprises at least two enzymatic treatments.

In one embodiment, the enzymatic treatment comprises treatment with alpha-amylase. In some embodiments, the treatment with alpha-amylase takes place at between 95 OC and 109 OC. In some embodiments, the treatment with alpha-amylase takes place at between 100 OC and 109 OC. In some embodiments, the treatment with alpha-amylase takes place at between 107 OC and 109 OC. In some embodiments, during the treatment with alpha-amylase, a high sheer force is applied to the mixture. In some embodiments the high sheer force is applied for a period of at least five minutes.

In one embodiment, the enzymatic treatment comprises treatment with amyloglucosidase. In a further embodiment, the treatment with amyloglucosidase comprises maintaining the mixture at a temperature between about 50 OC and about 60 OC for a period no greater than about one hour.

In one embodiment, prior to the enzymatic treatment, the mixture is heated to at least 135 OC. In a further embodiment, the mixture is heated to at least 140 OC. In a further embodiment the mixture is heated to at least 150 OC. In a further embodiment, the liquid is heated to between 150 OC and 160 OC. In some embodiments, this heating is combined with a reduction in the pH of said mixture. In some embodiments, this reduction is to a pH of between about 1.4 and 2.0. In a further embodiment, the reduction in pH is to between about 1.6 and 1.8. In some embodiments, the mixture is allowed to cool naturally prior to the enzymatic treatment.

In one embodiment, the at least one enzymatic treatment step comprises heating the mixture, and wherein the mixture is subsequently allowed to cool naturally.

In one embodiment, following the at least one enzymatic treatment, and prior to filtration, the mixture is allowed to stand for at least two weeks. In a further embodiment, following the at least one enzymatic treatment, and prior to filtration, the mixture is allowed to stand for at least four weeks. In a further embodiment, following the at least one enzymatic treatment, and prior to filtration, the mixture is allowed to stand for at least five weeks.

In one embodiment the degraded polysaccharides are degraded to 6DP.

In one embodiment, at least 92% of polysaccharides are degraded to 6 DP. In some embodiments, at least 95% of polysaccharides are degraded to 6 DP.

In one embodiment, the degraded polysaccharides are degraded to 5 DP.

In one embodiment, at least 92% of polysaccharides are degraded to 5 DP. In some embodiments, at least 95% of polysaccharides are degraded to 5 DP.

In one embodiment, the degraded polysaccharides are degraded to 4 DP.

In one embodiment, at least 92% of polysaccharides are degraded to 4 DP. In some embodiments, at least 95% of polysaccharides are degraded to 4 DP.

In one embodiment, the degraded polysaccharides are degraded to 1 DP.

In one embodiment, at least 92% of polysaccharides are degraded to 1 DP. In some embodiments, at least 95% of polysaccharides are degraded to 1 DP.

In one embodiment, after filtration the filtrate is diluted or concentrated so as to provide a mixture with a concentration of β-glucan of 2% w/w.

In one embodiment, after filtration the filtrate is diluted or concentrated so as to provide a mixture with a concentration of β-glucan of 1.5% w/w.

In one embodiment, after filtration the filtrate is diluted or concentrated so as to provide a mixture with a concentration of β-glucan of 1% w/w.

In one embodiment, the mean average size of the β-glucans in the mixture is about 800,000 Daltons.

Further features and advantages of the invention will become apparent from the following description of preferred embodiments of the invention, given by way of example only, which is made with reference to the accompanying drawings.

DETAILED DESCRIPTION OF CERTAIN INVENTIVE EMBODIMENTS

Figure 1:
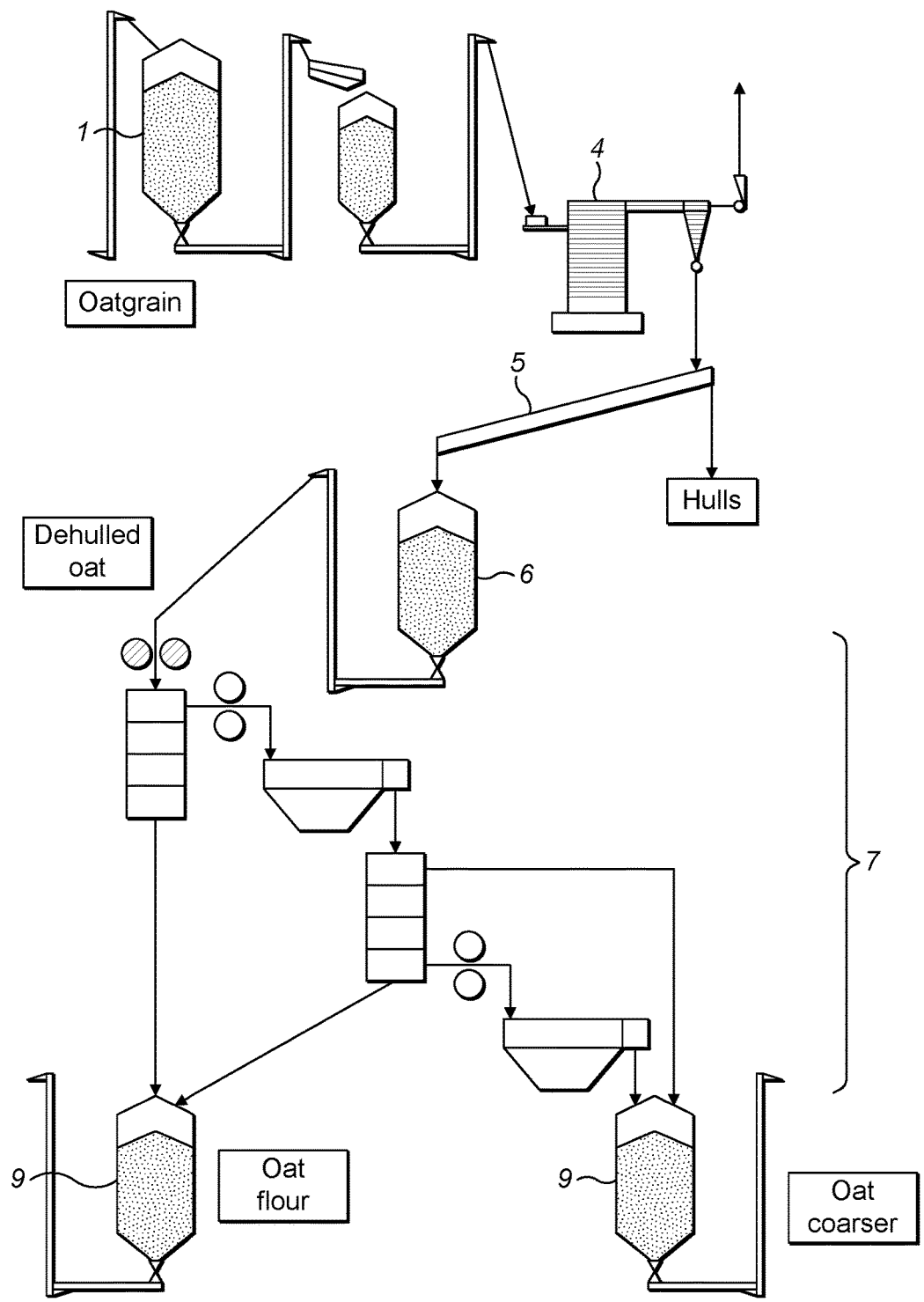
FIG. 1 shows an embodiment of a dry milling system which may be used in the production of the starting material for use in the methods of the invention.

The present invention provides a method for producing a liquid composition comprising β-glucan. The β-glucan composition is suitable for a range of uses, for example as a food additive, a nutritional supplement, in pharmaceutical compositions, in healthcare, for hair care, skin care and for use in cosmetics.

The present invention utilises a starting material comprising at least two polysaccharides, and no more than 5% of oil and no more than 1% of protein, wherein one of the polysaccharides is β-glucan, and wherein at least one polysaccharide is not β-glucan. To date, the availability of a starting material comprising β-glucan, at least one other polysaccharides and no more than 5% of oil and no more than 1% of protein has not been appreciated. However, it has been advantageously realised that intermediate products of processes for producing dried β-glucan provides a suitable starting material. In some embodiments, one or more of the polysaccharides in the starting composition may be dextrins. In some embodiments, the β glucan in the composition may comprise one or more of (1,3)-β-glucan, (1,4)-β-glucan and (1,3;1,4)-β-glucan. In particular, the composition may comprise (1,3;1,4)-β-glucan. Exemplary starting materials comprise between 8-9% dry matter, of which between 30% and 40%, for example approximately 35%, is β-glucan, with all or substantially all of the remainder of the dry material being maltodextrins; there may also be some residual protein.

Accordingly, a first aspect of the invention provides a method of processing a mixture comprising at least two polysaccharides, and no more than 5% of oil and no more than 1% of protein, wherein one of the polysaccharides is β-glucan, and wherein at least one polysaccharide is not β-glucan. The method comprises as a first step subjecting the mixture to at least one enzymatic treatment. The enzymatic treatment degrades at least a portion of at least one polysaccharides present in the mixture that is not β-glucan. This is followed by a second step of filtering the enzymatically treated mixture via means of membrane filtration. This results in a liquid β-glucan composition. This composition may be a solution, colloidal dispersion or a suspension. In some embodiments the composition will be a solution. In some embodiments the composition medium will be aqueous.

In some embodiments, the starting material comprises no more than 4% of oil. In some embodiments, the starting material comprises no more than 2% of oil. In some embodiments, the starting material comprises no more than 1% of oil.

The starting material may be diluted in order to reduce the concentration of β-glucan, for example by the addition of water. In one embodiment, the starting material is diluted to provide a concentration of β-glucan of approximately 1.5% or approximately 1.3%.

The optionally diluted starting material is subjected to at least one enzymatic treatment. Optionally, one or more enzymatic treatments may occur in a stirred reaction tank, to which the starting material is added either before or after any dilution.

The enzymatic treatment is conducted in order to at least partially degrade one or more polysaccharides other than the β-glucan. Any enzyme capable of catalysing the cleavage of polysaccharide bonds may be used; for example one or more enzymes selected from the amylase and amyloglucosidase enzyme groups may be used, for example, α-amylase and β-amylase. Generally, enzymes which do not degrade the β-glucans are preferred, for example alpha-amylase; however, one or more enzymes which degrade β-glucans may be used either instead of or in addition to other enzymes which degrade at least one polysaccharide but do not degrade β-glucan. Enzymes which degrade β-glucan may be used when it is desired to reduce the average size of the β-glucan molecules. In order to control the resultant size of the β-glucan molecules, the enzyme which degrades β-glucan must be added for a pre-determined period of time prior to quenching the reaction. Where other enzymatic treatments which do not degrade β-glucan are being used, the treatment with an enzyme which degrades β-glucan may overlap with a portion of at least one other enzymatic treatment. Alternatively, the treatment with an enzyme which degrades β-glucan may occur separately from the other enzymatic treatments.

The composition may be heated so as to improve enzyme activity, preferably before addition of the enzyme. The temperature to which the solution is heated will be determined by the specific enzymes used. In some embodiments one or more thermostable enzymes may be used. Whilst many enzymes derived from mesophiles will undergo significant denaturation at temperatures of 55° C. or more, with the rate of denaturation increasing with increased temperature, thermostable enzymes are enzymes which are more resistant to denaturation and so may retain effective, and in some cases optimal, activity at temperatures equal to or greater than 60° C., 70° C., 80° C., 90° C., 95° C. or more. For example, thermostable alpha-amylases are commercially available which are functional at temperatures of 95° C. and above. By using thermostable enzymes, the composition being subjected to enzymatic treatment can be heated to elevated temperatures such as 60° C., 70° C., 80° C., 90° C., 95° C. or more. In addition to optimising enzyme activity, such elevated temperatures can reduce microbial contamination, and can also prevent enzymatic activity from other, undesired enzymes. Such undesired enzymes may be present as contaminants in the enzyme used for enzymatic treatment, or may be present as a residual element from the cereal grain processed to produce the starting material. The process also proceeds more quickly at elevated temperatures.

The pH of the composition may also be modified to improve enzyme activity. The desirability of any change to pH will be dependent on the enzymes used, but for example the pH may be modified from between 6 and 7 to between 3.5 and 5 or to between 4.5 and 5. A variety of means known in the art may be used to achieve this.

The enzymatic reaction should be allowed to proceed for a time long enough to sufficiently degrade at least one polysaccharide so as to reduce flocking in the final product, for example for at least 30 minutes, 45 minutes, 1 hour, 2 hours, or more. In general, a period of between 1 and 2 hours is used, dependent upon the degree of degradation required. Dextrins will cause flocking at a DP (degree of polymerisation, i.e. the number of monomeric units in the polymer), of between 7 and 12, or more. Consequently, where at least one polysaccharide in the composition other than β-glucan is a dextrin, the dextrin may be degraded to about 6 DP, 5 DP, 4 DP or 1 DP, and the enzymatic treatment proceeds for at least long enough to obtain this degree of degradation. In many circumstances, no flocking will occur when a dextrin is degraded to below 4-5 DP, and so in some embodiments, the dextrins will be degraded to less than 5 DP or less than 4 DP. Likewise, where polysaccharides other than dextrins (or β-glucan) are present in the composition, the enzymatic treatment may be allowed to proceed for a time sufficient to degrade the polysaccharides to 6 DP, 5 DP, less than 5 DP, 4 DP, less than 4 DP, or 1 DP.

Once the enzymatic treatment has been allowed to proceed for a sufficient time, the enzymatic treatment should be stopped. This may be done by heating the composition to a temperature sufficient to denature the enzymes, for example, 80° C., 100° C., 120° C., 140° C. or greater. The temperature to which the composition must be heated to denature the enzyme will be dependent upon the specific enzyme. For example a thermostable alpha-amylase may need to be heated to 140° C., whereas if amyloglucosidase is being used without a thermostable alpha-amylase, the composition may need to be heated to 80° C. In some embodiments, the heating of the composition may be via means of a heat exchanger. For example, the composition may be heated for approximately 15 seconds at the desired temperature using a heat exchanger. Known methods for quenching enzymatic reactions other than heating may also be used.

In some embodiments, prior to the enzymatic treatment, the composition may be heated to at least 135° C. or more. This may be achieved, for example, via means of a heat exchanger. This enables the enzymatic degradation of resistant maltodextrins, which may otherwise not be degraded. The degradation of resistant maltodextrins prevents the small amount of flocking in the final product which may otherwise occur. In some embodiments, the composition is heated to at least 140° C., at least 150° C., or between 150° C. and 160° C. In some embodiments, this heating is combined with a reduction in the pH of the composition to between about 1.4 and 2.0, and preferably to between about 1.6 and 1.8. This facilitates the opening out of the resistant maltodextrin chains, to aid with their degradation. However, the low pH is not suitable for all end uses of the product, and so is not used in all circumstances.

In some embodiments, resistant maltodextrins are degraded by applying a high sheer force to the composition during the enzymatic treatment. In some embodiments, the treatment comprises alpha-amylase and a temperature of between 95° C. and 109° C., preferably between 100° C. and 109° C., and more preferably between 107° C. and 109° C. In some embodiments the high sheer force is applied for a period of at least five minutes. In some embodiments the use of a high sheer force during enzymatic treatment may be in addition to an earlier heating step to degrade resistant maltodextrins. The application of a high sheer force may be achieved by any means known in the art.

Where the composition has been heated, whether to denature enzymes or enable degradation of heat resistant maltodextrins, the composition may be allowed to cool naturally prior to filtration. This allows the composition to settle, reducing its turbidity. This means a more efficient, less expensive, filtration process may be used. Alternatively, the composition may be filtered immediately after heating, but the greater turbidity of the composition makes the filtration process more expensive. The composition may be allowed to stand for at least two, at least four or at least five weeks.

The composition is then filtered. A filter of between 0.45-1.5 µm, optionally 0.8-1.0 µm, may be used. Preferably, membrane filtration is used, although other means of filtration, for example sand filtration, may be used.

Before or after filtration, preservatives may be added to the composition; however, it is preferable for the preservatives to be added prior to filtration, as the warm, sugar rich composition is otherwise prone to microbial growth. Suitable preservatives comprise any of: phenoxyethanol (for example at a concentration of 0.2% to 1%), which is sold under the brand name Euxyl 701; benezoate (for example sodium benzoate, for example at a concentration of about 0.2% to 0.8%); 1,2 hexanediol (for example at a concentration of about 0.4%), caprylyl glycol (for example at a concentration of 0.4%), glycerine (a combination of benzoate, 1,2 hexanediol, carpylyl glycol, and glycerine is sold under the brand SymDiol); sorbates (for example potassium sorbate); and rosemary extract. It may be preferable to use only preservatives which are certified as being "natural", in order that the final product can be labelled as natural, in accordance with the labelling laws of many countries. Natural preservatives which may be used comprise SymDiol; 3% glycerine; and rosemary extract.

After filtration, and before or after any preservatives are added, the concentration of β-glucan in the composition may be adjusted by dilution. Products in which the final concentration of dry matter is between 1 and 8% may be produced. Generally, about one-third of the dry matter will be β-glucan and two thirds will be products resulting from the degradation of the other polysaccharides, e.g. sugars. Products with β-glucan concentrations of between about 0.35 and about 2.5% may be produced. However, gelling can occur in the product when β-glucan is present at a concentration of about 2% or more, and so compositions with a β-glucan concentration in the range of about 0.8 to about 1.8, and preferably about 1.0 to about 1.5% are preferred. The resultant product may have a viscosity of between 20-500 cps at 20° C., dependent upon the β-glucan content and the preservatives used. In some embodiments, the viscosity will be about 80-240 cps at 20° C., and in some embodiments of between 100-200 cps at 20° C. If a reduction in gelling is desired, this can be achieved through the use of anti-gelling additives, such as zwitterionic additives, and/or by using β-glucans with a lower molecular weight.

The resultant product is low in protein and oil and has good stability due to the reduction in flocking. In some embodiments, the resultant product will have a shelf life of at least 12, 18, 24, 30 or 36 months. Shelf life may be defined as a period during which there is no noticeable microbial growth, no hazing and no variation in viscosity.

In embodiments of the method, the process only comprises procedures and reagents which are deemed to be natural for labelling purposes, so that the resultant product can be labelled and marketed as a "natural product"; for example the resultant product may not contain parabens. The resultant product may be hypoallergenic.

The resultant product may be of use in foods, pharmaceuticals, cosmetics, hair care and skin care products.

The resultant product may be used to soothe skin. The resultant product may be used to reduce the appearance of skin redness, either alone or in combination with other skin care products such as retinol. The resultant product may be used to reduce the appearance of wrinkles and lines on the skin. The resultant product may be used to treat and/or provide relief from the symptoms of insect bites. The resultant product may be used to treat and/or provide relief from the symptoms of sun exposure, for example sunburn. The resultant product may be used as an ingredient in any of skin-care products, cosmetic products, and beauty products, for example: moisturisers, lotions, and creams, whether for application to any of the hands, face or body; sun-screens; after-sun formulations; eye serums; and soaps.

The resultant product may be used as an ingredient in mouth wash or toothpaste.

The resultant product may be used as an anti-irritant. The resultant product may be used as an ingredient in any of: shaving products, for example shaving creams, shaving gels, and lotions; underarm products, for example deodorants and anti-perspirants; and wipes, such as baby-wipes.

The resultant product may be used to facilitate wound healing.

The resultant product may be used in hair care to: improve tensile hair strength; increase the glossiness of the appearance of hair; and/or to moisturise the scalp. The resultant product may be used as an ingredient in any of shampoos, serums and conditioners, for example leave-in conditioners and leave-in serums.

The starting material, i.e. the mixture to be processed in the methods of the invention, can be derived from a number of sources. It may be derived from one or more types of cereal grain, for example, oat, wheat, barely or rye. Oats have a relatively high concentration of β-glucans and are preferred. In preferred embodiments the grain is not heat-treated.

The starting material may comprise one or more forms of water-soluble β-glucans. In some embodiments, the β glucan in the composition may comprise one or more of (1,3)-β-glucan, (1,4)-β-glucan and (1,3;1,4)-β-glucan. In particular, the composition may comprise (1,3;1,4)-β-glucan. The β-glucan may have an average size of less than 2,000,000 Daltons. The average size of the β-glucan in the starting material may be about 1,600,000, 1,200,000, 1,000, 000, 800,000, 600,000, 400,000 or less than 400,000 Daltons. The average size of the β-glucan in the starting material may be about 800,000 Daltons.

Methods for producing the starting material provide that de-hulled grain is dry milled to an endosperm-starch rich flour fraction and a coarser endosperm-reduced fraction. In some embodiments, between 45%-55% of the milled grain is retained in the coarser endosperm reduced fraction.

The endosperm-reduced fraction is dispersed in water and treated with a starch degrading alpha-amylase enzyme. The alpha-amylase may be a thermostable alpha-amylase, and the enzymatic hydrolysis may be performed at temperatures of about 95° C. or more. In some embodiments this may be followed by a second hydrolysis step using an enzyme, or combination of enzymes, from the group amyloglucosidases and pullulanases. The second hydrolysis step may be performed at for up to 40 minutes and at a temperature of 55° C. or greater. One or more of the enzyme treatments are optionally performed in combination with aqueous wet-milling. Where amyloglucosidase is used, the amyloglucosidase enzyme may be substantially cleaned of β-glucanase side activities prior to use, for example via a two-step procedure using anion exchange followed by hydrophobic interaction chromatography, the major protein band eluting from the hydrophobic interaction chromatography column being utilised as the cleaned enzyme A further step is enzyme inactivation by wet heat treatment, followed by the spontaneous or centrifugal separation of the hydrolysate mix into an aqueous top-layer rich in β-glucans, and a lower layer containing proteins, oils and the insoluble fibrous portion of the grain. The aqueous top layer may comprise more than 20% β-glucan on a dry matter basis. In some embodiments, the β-glucan may have a molecular weight of at least 400,000 Daltons, at least 800,000 Daltons, or at least 1,300,000 Daltons. This aqueous top-layer may then be used as a starting material for the present process.

In some embodiments, the hydrolysate spontaneously separates, or is optionally separated centrifugally, into 3 distinct layers, a top-layer which is rich in soluble dietary fibres, particularly β-glucans, but containing little oil (<2.5%) or protein (<7%), a middle aqueous layer, and a lower phase containing most of the protein, oil and insoluble fibrous material from the milled grain.

The aqueous top layer can be removed via the use of a decanter, for example a 2-phase or 3-phase decanter or other suitable device, yielding a soluble fraction which in some embodiments may contain at least 10% (on a dry matter basis) β-glucans, along with maltodextrins, arabinoxylans, sugars and relatively low amounts of protein (<7%) and oils (<2.5%).

The separated top layer rich in β-glucans can optionally be further treated via enzymatic hydrolysis, for example using one or more enzymes from the groups of lichenase, cellulase, and xylanase, in order to reduce the size of the β-glucan and/or fine tune its properties, in a controlled manner.

In some embodiments, the separated top layer may contain at least 10%, and in some embodiments up to 40% β-glucan, and not more than 10%, 7% or 5% protein, and less than 2.5%, 2.0%, 1.5%, or 1.0% oil, on a dry matter basis.

By way of a first example, a starting material may be prepared as follows: oat grain was first de-hulled and the de-hulled grains were dry milled and 50% by weight of the grain was retained as a coarser fraction. 575 g of this material was suspended in 4 liters of water at a temperature of 95° C., in a 5 liter reaction vessel fitted with a mechanical stirrer. Alpha-amylase enzyme (35 units) was added to the suspension and the mixture was incubated, with stirring and intermittent wet-milling, for 1 hour. After this time, the pH was dropped to 4.5, the temperature lowered to 75° C. and amyloglucosidase (AMG) enzyme was added (35 units), the mixture being incubated for 15 minutes with stirring. Enzymes were then completely de-activated by heating of the suspension in an autoclave at 140° C. for some minutes.

The resulting suspension was then centrifuged, producing three distinct layers which were separated and collected: an aqueous top layer rich in soluble dietary fibre, particularly β-glucan, dextrins and sugars, in particular maltose and maltotriose, <1% fat, and <3% proteins, a protein-oil rich layer and a bottom layer containing the insoluble fibrous part of the milled oat. The yields of top layer, protein-oil fraction and the fibre fraction were 15%, 15% and 20.0% respectively (on a dry matter basis). The remainder was mostly soluble sugars and dextrins. The aqueous top layer rich in soluble dietary fibre can then be used as a starting material for the present process.

A second example of the production of a starting material is as follows: barley grain was dry milled to remove excess endosperm material and 50% of the milled grain, representing the coarser fraction, was utilized as the raw material for the trial. 575 g of this material was suspended in 4 liters of water at a temperature of 95° C., in a 5 liter reaction vessel fitted with a mechanical stirrer. Alpha-amylase enzyme (35 units) was added to the suspension and the mixture was incubated, with stirring and intermittent wet-milling, for 1 hour. After this time, the pH was dropped to 4.5, the temperature lowered to 75° C. and amyloglucosidase enzyme was added (35 units), the mixture being incubated for 15 minutes with stirring. Enzymes were then completely deactivated by heating of the suspension in an autoclave at 140° C. for some minutes. The resulting suspension was then centrifuged, producing three distinct layers which were separated and collected: an aqueous top layer rich in soluble dietary fibre, particularly β-glucan, a protein-oil rich layer and a bottom layer containing the insoluble fibrous part of the milled oat. The aqueous top layer rich in soluble dietary fibre can then be used as a starting material for the present process.

In a third example, starting material as prepared in example 1 was used. 150 kg of this material was added to 1050 liters of water at 95° C. in a 2,000 liter tank fitted with mechanical stirring. Alpha-amylase enzyme (9100 units) was added to the suspension and the mixture was incubated, with stirring and intermittent wet-milling, for 1 hour. After this time, the pH was dropped to 4.5 using 84% orthophosphoric acid, the temperature lowered to 75° C. and amyloglucosidase enzyme was added (9000 units), the mixture being incubated for 15 minutes with stirring. Enzymes were then completely de-activated by heating the resultant suspension by passing through a tubular heat exchanger at 140° C. The partially cooled hydrolysate suspension was then pumped into a 3-phase decanter and three fractions were obtained: a viscous top-layer rich in soluble dietary fibres, an aqueous fraction and a fraction containing most of the protein, fat and insoluble fibre from the milled oat grain. The separated top layer was then further diluted with water (1 part to 5 parts water), stirred and then excess protein removed centrifugally. The resultant supernatant can then be used as a starting material for the present process.

In a fourth example, a trial equivalent to that described in example 1 was performed and excess residual protein was then removed centrifugally.

In a fifth example, starting material was prepared as follows: oat grain was first de-hulled and the de-hulled grains were dry milled and 50% by weight of the grain was retained as the coarser fraction. 575 g of this material was suspended in 4 liters of water at a temperature of 95° C., in a 5 liter reaction vessel fitted with a mechanical stirrer. Alpha-amylase enzyme (35 units) was added to the suspension and the mixture was incubated, with stirring and intermittent wet-milling, for 1 hour. After this time, the pH was dropped to 5.3, the temperature lowered to 65° C. and pullulanase enzyme was added (35 units), the mixture being incubated for 30 minutes with stirring. Enzymes were then completely de-activated by heating of the suspension in an autoclave at 140° C. for some minutes.

The resulting suspension was then centrifuged, producing three distinct layers which were separated and collected: a viscous top layer rich in soluble dietary fibre, particularly β-glucan, a protein-oil rich layer and a bottom layer containing the insoluble fibrous part of the milled oat. The top layer rich in soluble dietary fibre can then be used as a starting material for the present process.

In a sixth example, the top layer isolated from oat in example 1 was further treated using an amyloglucosidase enzyme preparation which was cleaned of β-glucanase side activity as follows: 2 ml of amyloglucosidase was first passed through a column containing anion exchange resin (Bio-Rad AG 1-X4) equilibrated in 25 mM phosphate buffer, pH 5.8. Bound protein was then eluted from the column by application of a linear sodium chloride gradient, from 0 to 1 M. The major protein band was collected and re-concentrated to 2 ml using a 1000 Dalton ultrafilter. The partially cleaned enzyme was then passed onto a column containing hydrophobic interaction chromatography support material (Bio-Rad Macro-Prep t-Butyl HIC Support), equilibrated using 50 mM phosphate buffer, pH 6.0, containing 1.5 M ammonium sulphate. Bound enzyme was then eluted from the column by application of a linear decreasing gradient of ammonium sulphate from 1.5 M to 0. The major protein band eluting from the column was collected, concentrated to 2 ml using a 1000 Dalton ultrafilter and then utilised as cleaned amyloglucosidase.

100 ml of the top layer rich in β-glucan (on a dry matter basis) and total 6% dry matter, was diluted to 200 ml with deionised water in a Pyrex beaker, pH being adjusted to 4.6. The sample was placed in a water bath at 60° C., with magnetic stirring, and 100 μl of the cleaned amyloglucosidase was added to the mix. Incubation was carried out for two hours, after which time the sample was heated to 120° C. in an autoclave, to deactivate the enzyme. The sample can then be used as a starting material for the present process.

In a seventh example, a procedure equivalent in most respects to that described in example 6 was performed, using the same raw material, with the further addition of a xylanase enzyme preparation (50 μl) to the solution 15 minutes before the end of the incubation period (i.e. after 105 minutes).

Other methods can be used for producing the starting material. One or more types of cereal grain, for example, oat, wheat, barely or rye, may be used, preferably oats. In preferred embodiments the grain is not heat-treated, and in particular may comprise oats which have not been heat treated.

The grain is dehulled via conventional means, for example via the use of peelers. Unhulled grain is then separated from the dehulled grain. This can be achieved by the grain being passed to a shaking table. Air classification may then be applied to suck the hulls up and away from the dehulled grain. In one embodiment, the dehulled grain is permitted to comprise up to 16 unhulled grains per 100 g of dehulled grain. Preferably, the dehulled grain may be permitted to comprise up to 1% of unhulled grains per dehulled grain; a percentage of unhulled grains may be used, but this will decrease potential yields. Preferably, the number of unhulled grains per 100 g of dehulled grain is equal to or greater than 10, so as to avoid excessive loss of dehulled grains.

Preferably, at least 85% of the grain is dehulled in a single cycle through the peelers. The unhulled grains which are recovered from the process may be passed back to the peelers.

The unhulled grain is then milled. In one embodiment milling is performed via use of a disk mill. A disk mill may be used even when oat grains are being milled. Preferably, the grains are milled to an extent sufficient to ensure that between about 20% and 25% of the endosperm is retained with the bran, as this provides a good balance between ensuring a high recovery of β-glucan whilst limiting the amount of starch retained in the bran. In one embodiment, the space between the disks in the disk mill is set at about 1.75 mm. The space between the disks may be optimised depending upon the crop being milled. In one embodiment, the space between the disks in the disk mill is set to provide milling of the grain sufficient to ensure that between about 20% and 25% of the endosperm is retained, particularly when oat grains are being milled.

In another embodiment the milling is performed by means of a roller mill. A roller mill will produce less variability than the disk mill. This allows for greater optimisation of subsequent sifting and milling, which enables greater precision in the subsequent enzymatic processes, due to greater consistency of the characteristics of the bran. In particular, the use of a roller mill decreases the likelihood of smaller oat grains passing through the mill and into the bran without being milled, which would otherwise increase the amount of starch in the bran.

In some embodiments the distance between the rollers in the roller mill may be determined on an ongoing basis. This has the advantage of being able to adjust for natural variances within the grain. In one embodiment, the distance can be determined by sporadically taking a sample of the fraction output by the roller mill and running it through a series of stacked sieves.

The milled grains are then optionally passed through a sifter. In one embodiment, the sifter is a vertical sifter. In one embodiment, the size of the mesh in the vertical sifter may be between about 1.6 mm and 1.8 mm, and preferably about 1.75 mm. Alternatively a horizontal sifter may be used. It has been discovered that a larger gap between the mesh and the outer wall may be advantageous when milling oats as this reduces the clogging which may otherwise occur, due to the stickiness of the oats. A sifter with a larger gap may therefore require less cleaning when milling oats. Horizontal sifters tend to have a larger gap between the mesh and outer wall than comparable vertical sifters. A horizontal sifter may therefore require less cleaning than a vertical sifter when milling oats.

By passing the milled grain through a sifter, two fractions are produced, a small fraction and a large fraction. The large fraction is passed to a roller mill (which will be a second, distinct roller miller in embodiments in which the initial milling was conducted by a roller mill), wherein the roller mill presses the large fraction. Where a sifter is not used, the milled grain is passed to a roller mill.

The small fraction from the sifter is passed through one or more first sieves in order to remove the flour whilst retaining the small grain fractions. In some embodiments, one or more first sieves are rotary sieves. In some embodiments, the meshes may comprise nylon and/or other artificial fibres. An artificial fibre is one which does not predominantly comprise a naturally occurring fibre. Artificial fibres may be polymers produced from petrochemicals. The use of nylon or other artificial fibres can be advantageous due to the increased vibrations of the mesh, which prevents sticking. This is particularly advantageous when milling oats, as oats have a higher proportion of lipids in comparison to most other grains, and so are more prone to sticking. This means the mesh sizes for meshes comprising nylon and/or other artificial fibres can be smaller. In embodiments in which the first sieves comprise nylon and/or other artificial fibres may have a mesh with a size between about 300 and 700 μm, more preferably between about 310 and 600 μm, more preferably between about 320 and 500 μm, more preferably about 330-400 μm, and more preferably about 350-370 μm. The ability conferred by the use of meshes comprising artificial fibres means that the ability to remove starch-containing flour is not impaired by clogging of the mesh, whilst ensuring that more of the β-glucan comprising material is retained. Consequently, an oat bran fraction with proportionally less starch, i.e. a lower percentage of starch on a dry matter basis, can be produced.

In some embodiments multiple first sieves may be used to ensure sufficient throughput of the small fraction. In some embodiments, two first sieves may be used.

In some embodiments the fraction retained by the one or more first sieves may then be passed to a final sieve. In other embodiments, the fraction retained by the one or more first sieves may then be passed to a further (third) sieve. In other embodiments, the fraction retained by the one or more first sieves is then joins the large fraction stream from the sifter, before being passed to the rotary mill. Preferably, the rotary mill will be configured so as to press the large fraction, but not the fraction retained by the first sieves as pressing of the fraction retained by the one or more first sieves can reduce the β-glucan yield.

In some embodiments the distance between the rollers in the roller mill may be determined on an ongoing basis. This has the advantage of being able to adjust for natural variances within the grain. In one embodiment, the distance can be determined by sporadically taking a sample of the fraction output by the roller mill and running it through a series of stacked sieves. The desired profile may be determined based on the equipment used for downstream processing, for example wet milling, as the size profile of the contents of the fraction output roller mill can have an impact on the wet milling process.

The fraction output by the roller mill is then passed through one or more second sieves. Optionally, multiple second sieves may be used to improve throughput. Optionally two or more second sieves are used. In some embodiments the first second sieve may have a mesh size of about 1.6 mm, and the second sieve may have a mesh size of between about 350 and 400 microns. The use of a first second sieve with a larger mesh size than the second second sieve prevents blockage of the second second sieve. The first second sieve may also agitate or smash the bran so as to remove flour stuck to the bran. In an embodiment, the first second sieve is a roller mill.

In some embodiments, the small fraction from the one or more second sieves is then passed to the third sieve. In other embodiments, the small fraction from the one or more second sieves is then returned to the fraction retained from one or more first sieves and passes through the rotary mill again.

In embodiments in which at least one of the large fraction from the first sieve and the small fraction from the second sieve are passed to the third sieve, the third sieve will remove flour from the fraction, producing a coarse fraction which may then pass to the final sieve.

Optionally, the large fraction from one or more second sieves may pass through one or more repetitions of roller millers and one or more sieves. With each repetition, the small fraction from the one or more sieves is passed back to an earlier roller mill in the process; preferably the small fraction from the one or more sieves is returned to the fraction retained from one or more first sieves.

After the final repetition of milling and sieving, the large fraction retained by the sieve is passed through a final sieve, to remove any remaining flour. Preferably, the final sieve may comprise one or more artificial fibres. In some embodiments, the final sieve may have a have a mesh size of between about 150 and 200 microns; in some embodiments the mesh size of the final sieve may be between about 170 and 185 microns. The fraction retained by the final sieve is conveniently referred to as the bran fraction, but will comprise bran and parts of the aleurone layer and sub-aleurone layer.

In some embodiments, the bran fraction will constitute between 30 and 55%, and preferably between 35-45% of the original grain. More preferably the bran fraction will constitute between 35-40% of the original grain and the remainder may be between 28-35% or 35-40% husk and between 25-32% or 25-30% flour, respectively.

Advantageously, the use of the above described dry milling process results in an oat-bran fraction with a lower proportion of starch. This enables increased efficiency in downstream processing, such as enzyme degradation, alkali extraction and alcohol precipitation. For example, in processes in which the starch is subjected to enzymatic degradation, a lower proportion of starch in the oat bran fraction enables a shorter period of enzymatic degradation to be utilised, which provides a more efficient overall process, both in terms of speed of production and cost of production, particularly where the process of enzymatic degradation occurs at an elevated temperature, as reducing the length of time for which an elevated temperature is maintained reduces the cost of processing. Reduced starch in the oat bran fraction also provides advantages following enzymatic degradation, as there will be less sugar in the slurry post-degradation. This enables more efficient separation of components within the slurry, and also more efficient drying of the components, as an excess of starch and starch derivatives, such as dextrins, maltodextrins and sugars, can cause clogging within the machinery used for separation; this is particularly evident where continuous processes, such as continuous centrifugal separators are utilised. The reduction in starch also means that less enzyme can be used in the process, thereby providing a cost saving. Less water may also be used in the process, which again results in efficiencies in heating, as a lower volume requires heating, and also provides an improvement in efficiency as less drying is required. With a reduction in starch smaller equipment can be used.

The ability of the above-described dry-milling process to reduce the proportion of starch in the oat bran fraction is shown in Table 1, below. Fractions 1-7 were produced using a process as described above, in which the initial milling was performed by a roller mill, a horizontal sifter was used, and first and second rounds of sieves with a further intermediate roller milling were utilised, with the meshes of the first sieves and second sieves comprising nylon with a mesh size of between about 300 and 420 μm. Fractions 8-17 were produced by a process similar to that described above, but a disk mill was used for the initial milling, a vertical sifter was utilised, and only a single round of sieving was used, in which a metal mesh with a mesh size of approximately 450 μm was utilised.

| Fraction Number | Mesh type used | % starch in oat bran fraction on a dry matter basis |
|---|---|---|
| 1 | Nylon with a mesh size of between about 300 and 420 μm | 42.9 |
| 2 | Nylon with a mesh size of between about 300 and 420 μm | 42.4 |
| 3 | Nylon with a mesh size of between about 300 and 420 μm | 43.2 |
| 4 | Nylon with a mesh size of between about 300 and 420 μm | 43 |

-continued

| Fraction Number | Mesh type used | % starch in oat bran fraction on a dry matter basis |
|---|---|---|
| 5 | Nylon with a mesh size of between about 300 and 420 μm | 42 |
| 6 | Nylon with a mesh size of between about 300 and 420 μm | 43 |
| 7 | Nylon with a mesh size of between about 300 and 420 μm | 38 |
| 8 | Metal with a mesh size of about 450 μm | 47 |
| 9 | Metal with a mesh size of about 450 μm | 48 |
| 10 | Metal with a mesh size of about 450 μm | 50 |
| 11 | Metal with a mesh size of about 450 μm | 50 |
| 12 | Metal with a mesh size of about 450 μm | 48 |
| 13 | Metal with a mesh size of about 450 μm | 46 |
| 14 | Metal with a mesh size of about 450 μm | 46 |
| 15 | Metal with a mesh size of about 450 μm | 50 |
| 16 | Metal with a mesh size of about 450 μm | 47 |
| 17 | Metal with a mesh size of about 450 μm | 48 |

Given that the starting material, oat grains, are a naturally occurring product, there will be some inevitable natural variation in the levels of starch produced. Nevertheless, the figures in Table 1 demonstrate that the use of the herein described improved process produces an average proportion of starch in the oat bran fraction of 42% on a dry matter basis, as opposed to an average percentage of 48%, a reduction of 12.5%.

The oat bran fraction may comprise one or more forms of water-soluble β-glucans. In some embodiments, the β-glucan in the oat bran fraction may comprise one or more of (1,3)-β-glucan, (1,4)-β-glucan and (1,3;1,4)-β-glucan. In particular, the oat bran fraction may comprise (1,3;1,4)-β-glucan.

Oat bran fractions with reduced starch according to the present invention may be used in a number of downstream processes.

The bran fraction is then subjected to a process of enzymatic degradation. The bran fraction is dispersed in water and treated with a starch degrading alpha-amylase enzyme.

In some embodiments, the bran fraction is mixed with water prior to the addition of any enzymes (although some enzymes native to the oat grain may already be present in the bran fraction). In some embodiments, this may be done in a separate vessel, such as a pre-reactor tank, to that in which enzymatic degradation will occur. The use of a separate vessel can provide greater control over the amount of bran fraction being subjected to enzymatic degradation, as in embodiments in which the bran fraction is added directly to the reaction vessel, a blockage or inconsistency in the rate in which bran is added can lead to greater variation in the end-product, particularly if the blockage or inconsistency is not noticed by the operator, for example if the blockage clears without operator intervention, and/or the inconsistency is only present for a short period of time. Alternatively, the alpha-amylase enzyme may be added at the same time as the water and bran; this may cause an increase in fat content in the downstream processes, and so may be done where an increase in fat in the beta-glucan stream is desired. Without wishing to be bound by any theory, it is possible that the mixing of the bran with water and alpha-amylase causes some beta-glucan molecules to come out of solution, which then bind to the fat molecules, whereas when the enzyme is not added until after the bran-fraction is mixed with water, the fat may bind to the protein and so is removed along with the protein. Where there is excess fat present in the beta-glucan stream, this can cause problems in drying the beta-glucan; for example where a drum drier is used, excess fat may cause the beta-glucan to fall off the drum.

When adding the water to the bran fraction, the water may be pre-heated, for example to a temperature of between about 85° C. and about 95° C., e.g. to above about 90° C. or to between about 92.5° C. and about 95° C. This can increase the amount of beta-glucan revered, and may also reduce the binding of fat to beta-glucan and so reduce the level of fat in the downstream beta-glucan stream in embodiments in which that is desirable.

In embodiments in which the water and bran fraction are mixed prior to the addition of the alpha-amylase, and/or the water and bran fraction are mixed in a separate vessel, the mixing may be for a pre-determined period of time prior to the addition of the alpha-amylase and/or the movement of the resultant slurry to the reactor vessel. The pre-determined period of time may be for at least about 5 minutes, or at least about 10 minutes.

The alpha-amylase may be a thermostable alpha-amylase, and the enzymatic hydrolysis may be performed at temperatures of about 95° C. or more. In some embodiments this may be followed by a second hydrolysis step using an enzyme, or combination of enzymes, from the group amyloglucosidases and pullulanases. The second hydrolysis step may be performed at for up to 40 minutes and at a temperature of 55° C. or greater. Where amyloglucosidase is used, the amyloglucosidase enzyme may be substantially cleaned of β-glucanase side activities prior to use, for example via a two-step procedure using anion exchange followed by hydrophobic interaction chromatography, the major protein band eluting from the hydrophobic interaction chromatography column being utilised as the cleaned enzyme.

One or more of the enzyme treatments are optionally performed in combination with aqueous wet-milling. For example, in some embodiments enzymatic hydrolysis may be performed in a series of reactor vessels, with a wet mill interspersed between the reactor vessels. Wet milling the slurry opens up new surfaces on which the enzymes can operate.

Following enzymatic degradation, the resultant slurry is separated. In some embodiments, this may be done by means of centrifugation in order to produce between 2 and 4 distinct layers, including an aqueous top-layer rich in β-glucans, and a lower layer containing proteins, oils and the insoluble fibrous portion of the grain. The aqueous top-layer rich in β-glucans may then be removed, for example via use of a decanter, and used a starting material for the present process.

In some embodiments, the hydrolysate spontaneously separates, or is optionally separated centrifugally, into 3 distinct layers, a top-layer which is rich in soluble dietary fibres, particularly β-glucans, but containing little oil (<2.5%) or protein (<7%), a middle aqueous layer, and a lower phase containing most of the protein, oil and insoluble fibrous material from the milled grain.

The aqueous top layer can be removed via use of a decanter, for example a 2-phase or 3-phase decanter or other suitable device, yielding a soluble fraction which in some embodiments may contain at least 10% (on a dry matter basis) β-glucans, along with maltodextrins, arabinoxylans, sugars and relatively low amounts of protein (<7%) and oils (<2.5%).

As an alternative to centrifugation into distinct layers, the solid part of the slurry may be removed from the liquid part. Any suitable means of separation may be used. In some embodiments this may be achieved via the use of continuous centrifugal separators, in which the slurry is passed into a rotating chamber such that the solid part of the slurry accumulates on the walls of the chamber, with the liquid part of the slurry passing out of the separator.

The protein is then removed from the liquid part of the slurry. In some embodiments, this may be achieved by passing the liquid part of the slurry to a decanter in order to remove the protein as a paste from the remaining aqueous solution of β-glucans. The remaining aqueous solution comprising β-glucans may then be used as a starting material for the present process.

A heat-treatment may be used to deactivate the enzymes used in the process. This may occur immediately after the completion of enzymatic degradation, or may occur at any point following the enzymatic degradation, including following centrifugation, separation or decantation. Applying a heat treatment immediately following enzymatic degradation may be preferred in some embodiments, as this will enable greater control of the degree of degradation.

The aqueous solution of β-glucan may comprise more than 20% β-glucan on a dry matter basis. In some embodiments, the β-glucan may have a molecular weight of at least 400,000 Daltons, at least 800,000 Daltons, or at least 1,300,000 Daltons.

The aqueous solution of β-glucan can optionally be further treated via enzymatic hydrolysis, for example using one or more enzymes from the groups of lichenase, cellulase, and xylanase, in order to reduce the size of the β-glucan and/or fine tune its properties, in a controlled manner.

In some embodiments, the aqueous solution of β-glucan may contain at least 10% and up to 40% β-glucan, and not more than 10%, 7% or 5% protein, and less than 2.5%, 2.0%, 1.5%, or 1.0% oil, on a dry matter basis.

Figure 2:
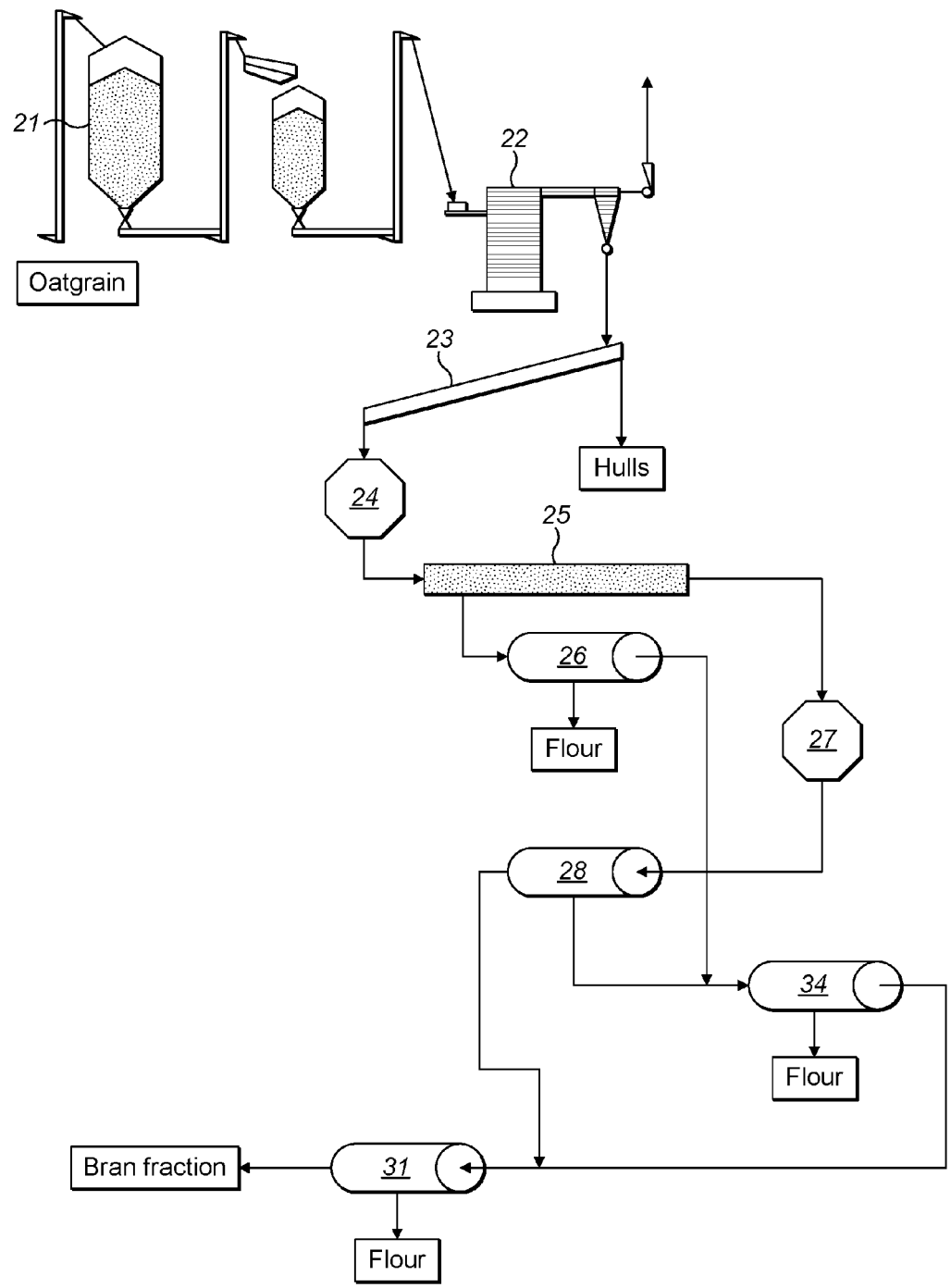
FIG. 2 shows an embodiment of a dry milling system which may be used in the production of the starting material for use in the methods of the invention.
Figure 3:
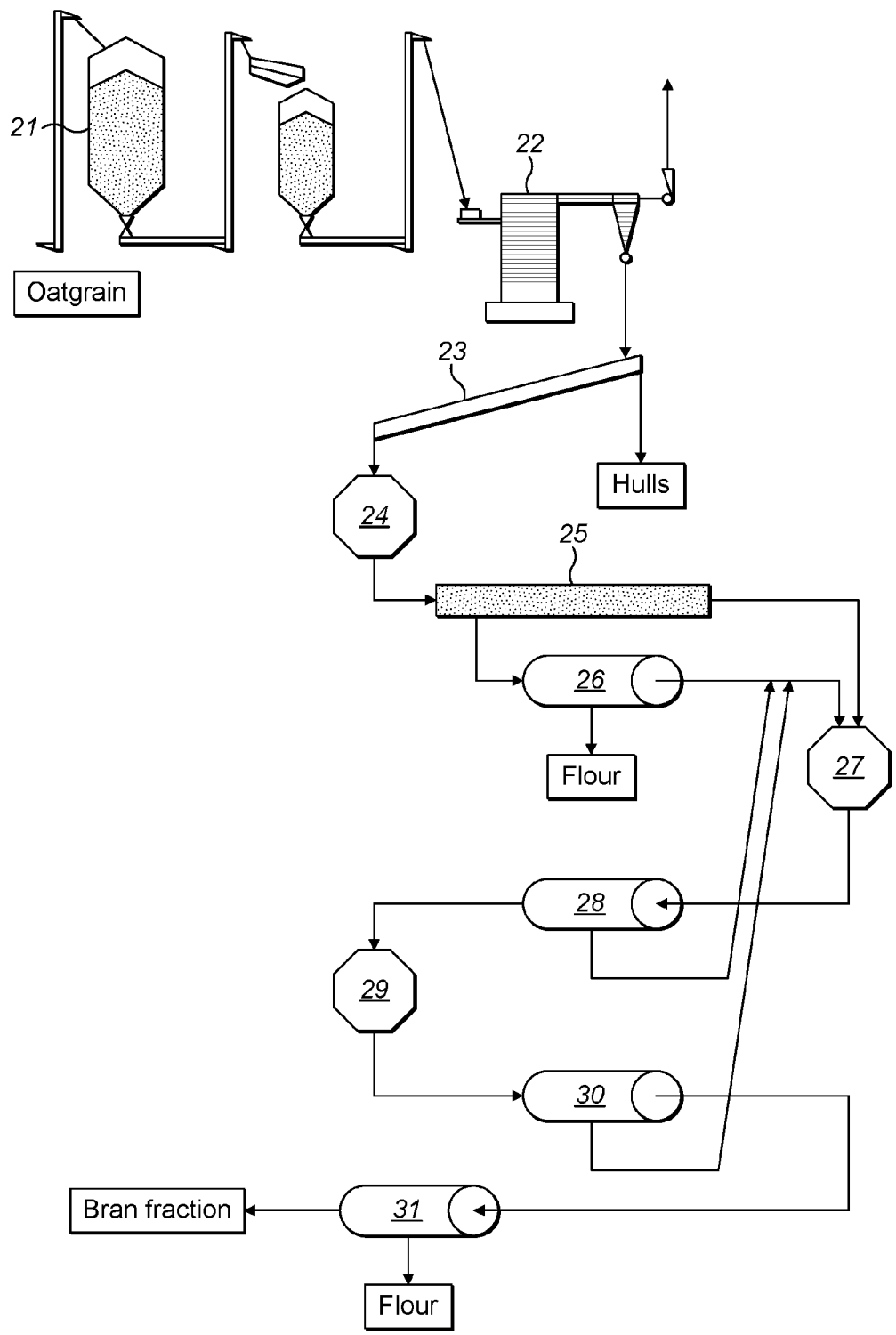
FIG. 3 shows an embodiment of a dry milling system which may be used in the production of the starting material for use in the methods of the invention.

FIGS. 1, 2 and 3 show a schematic overview of aspects of systems which may be used to produce a starting material in the methods described above.

FIG. 1 displays an embodiment of a dry milling system, and consists of a bin 1 for storing oat or barley prior to use. The grains are transported to a dehulling apparatus 4, where hulls are taken off via separator 5. The dehulled grains are transferred, via a bin 6, to a mill comprising milling rolls and sieves, generally denoted 7, from where flour is retained in a bin 8, and the coarser fraction is transferred to and retained in a bin 9 for further treatment.

FIG. 2 displays an embodiment of a dry milling system, and consists of a bin 21 for storing oat prior to use. The grain is transported to peelers 22 which dehull the grain. An air classifier (not shown) separates the hulls from the dehulled grain. The dehulled grain move to a shaking table 23 to separate out remaining unhulled grains. The grain then passes to a first roller mill, 24, where it is milled. The milled grain then passes to sifter 25, to produce a large fraction and a small fraction. The large fraction is passed to second roller mill 27, whilst the small fraction is passed to first rotary sieve 26. First rotary sieve 26 enables flour to be removed from the small grain fraction, whilst the large fraction from this first rotary sieve passes to third rotary sieve 34.

The milled product of second roller mill 27 passes to a second rotary sieve 28. The small fraction from this second rotary sieve 28 is then passed to third rotary sieve 34. This third rotary sieve removes flour from the fraction passing through it, with the large fraction produced by the third rotary sieve passing to fourth rotary sieve, 31

The large fraction retained by second rotary sieve 28 passes to the fourth rotary sieve, 31. This removes flour from the fraction passing through it, with the large fraction produced by this fourth rotary sieve is the oat bran fraction, and is suitable for downstram processing, for example treatment by enzymatic hydrolysis.

FIG. 3 displays an alternative embodiment of a dry milling system, and consists of a bin 21 for storing oat or barley prior to use. The grain is transported to peelers 22 which dehull the grain. The hulls and dehulled grain move to a shaking table 23 to separate the hulls from the grain.

The grain then passes to a first roller mill, 24, where it is milled. The milled grain then passes to horizontal sifter 25, to produce a large fraction and a small fraction. The large fraction is passed to second roller mill 27, whilst the small fraction is passed to first rotary sieve 26. First rotary sieve 26 enables flour to be removed from the small grain fraction. Having passed through first rotary sieve 26, the small grain fraction is then also passed to second roller mill 27. The milled product of second roller mill 27 is then passed to a second rotary sieve 28. The small fraction from this second rotary sieve 28 is then returned to the small grain fraction retained by first rotary sieve 26 before being passed into second roller mill 27.

The large fraction retained by second rotary sieve 28 is then passed to third roller mill 29. The milled product of third roller mill 29 then moves to third rotary sieve 30. The small fraction produced by third rotary sieve 30 is then passed back to the stream comprising the retained small grain fraction from first rotary sieve 26, before being passed to second roller mill 27.

The large fraction retained by third rotary sieve 30 is then passed to a fourth rotary sieve, 31. This removes flour from the large fraction. The retained large fraction, is the "bran fraction", and is suitable for treatment by enzymatic hydrolysis.

Figure 4:
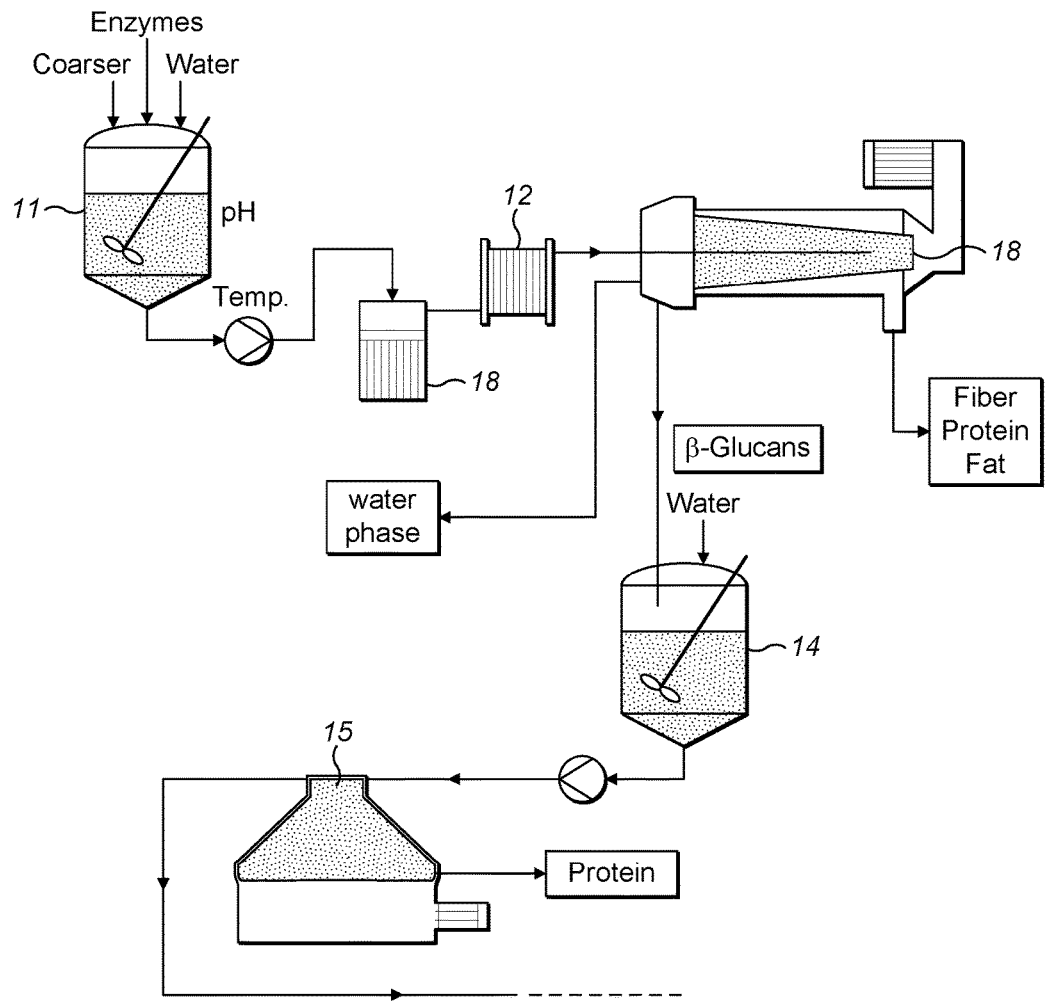
FIG. 4 shows an embodiment of a wet system which may be used in the production of the starting material for use in the methods of the invention.

The coarser fraction ("bran fraction") from FIG. 1, FIG. 2 or FIG. 3 may then be transferred to a wet system as depicted in FIG. 4, where it is introduced in a reaction vessel 11, together with the enzymes used and water to provide a slurry. A pH control sensor (not shown) is applied to the reaction vessel as well as a heating jacket or other temperature controlling means (not shown). The reacted mixture is transferred via a wet-mill 18 and a heat exchanger 12 to a separator 13 in the form of a decanter, where the top fraction/layer is transferred to a further reaction vessel 14, where the top layer is mixed with water to wash the product by separating of any entrapped protein being removed in a decanter 15. The aqueous top layer may then be used as a starting material for the present process.

Figure 5:
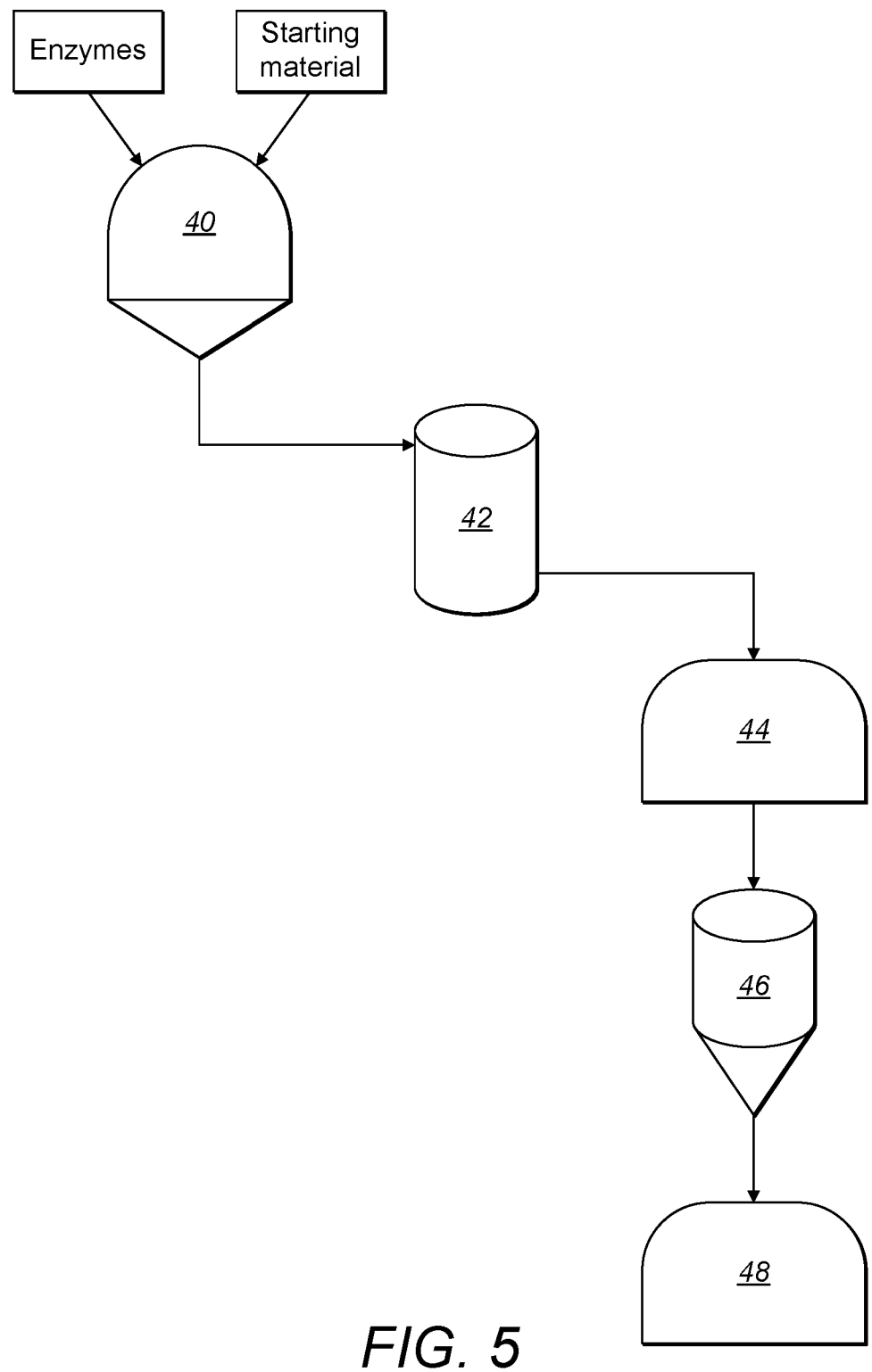
FIG. 5 shows a schematic overview of aspects of a system which may be used to perform methods of the present invention.

FIG. 5 shows a schematic overview of aspects of a system which may be used to perform methods of the present invention. The starting material is placed into reaction vessel 40. Optionally, water is added (not shown) to dilute the starting material to provide a desired concentration of β-glucans. Optionally, the starting material is treated with acid or other means of modifying the pH (not shown) to enable a desired pH to be reached. The optionally diluted starting material is then heated to a desired temperature. Once the desired temperature, and, if applicable, pH, have been reached, one or more enzymes are added to reaction vessel 40. If multiple enzymes are being used they may be added simultaneously or sequentially, with the period between the addition of the enzymes being determined in accordance with desired degree or degradation by each enzyme.

After the addition of the one or more enzymes, enzymatic degradation is allowed to proceed for a period of time sufficient to enable the desired degree or degradation to occur. The composition in reaction vessel 40 is then passed to heat exchanger 42. The reaction mixture is then heated to a temperature sufficient to denature the one or more enzymes. Optionally, the composition may be heated to a temperature of 150° C. or more in order to degrade heat resistant maltodextrins.

After passing through heat exchanger 42, the composition moves to tank 44, and optionally, preservatives are added. Here, the composition is allowed to cool naturally and allowed to settle for a desired period of time, for example two, four or five weeks.

Once sufficiently settled, the composition then passes to membrane filtration system 46 and is membrane filtered. The composition then moves to tank 48, where optionally preservatives (or further preservatives) may be added, and the concentration of β-glucan be adjusted. The resultant liquid composition comprises β-glucan, and is low in oil and protein.

Clinical studies have been conducted as to the effects of liquid compositions produced according to the present invention.

Trial 1: Reduction in Skin Irritation

In order to study and quantify the ability of liquid compositions produced in accordance the methods of the invention, five subjects between the ages of 23 and 54 were inducted into this study. The inner forearm region, midway between the wrist and elbow, was designated as the test area. Two 2 cm by 2 cm (4 $cm^2$) test sites were delineated using a gentian violet surgical skin marker and standard template. During the initial visit 1.5% Sodium Lauryl Sulfate (SLS) diluted in distilled water was applied in order to irritate the skin (induced erythema) on both test sites. 0.2 ml of 1.5% SLS was dispensed onto the occlusive, hypoallergenic patch. The patch was applied directly to the test sites located on the right and left forearm and the subject was dismissed with instructions not to wet or expose the test area to direct sunlight. After 24 hours the Study Director removed the patch and the grade of skin irritation was determined. Treatment with a liquid composition produced in accordance with the methods of the invention was assigned to site 1 (left forearm) while site 2 (right forearm) was left untreated as a control. Each panellist was asked to apply the test product to the designated test site twice daily (AM and PM). The first application took place at the test facility 15 minutes after SLS saturated patch removal. In order to assure the right amount of the test product (2 mg/$cm^2$) was delivered to the test site, each panellist was provided with three syringes filled with the product to the required volume. In order to monitor skin irritation reduction, panellists were evaluated at baseline and again after 2, 8 and 24 hours after initial application of the test material. Responses were evaluated objectively via grading performed by the trained technician using a scale of 0 (no evidence of any effect) to 4 (deep red erythema with or without vesiculation or weeping).

Figure 6:
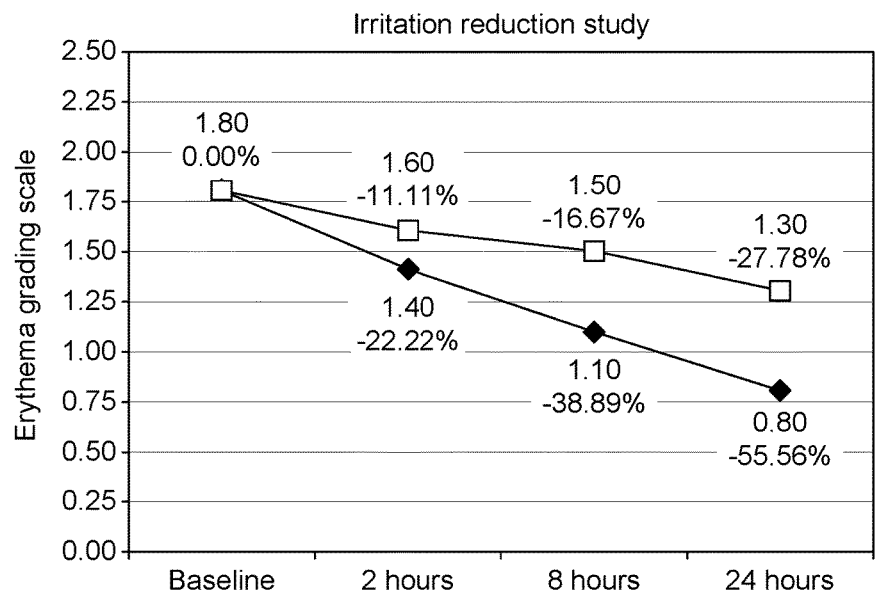
FIG. 6 shows the results of a clinical trial to determine the effectiveness in reducing skin irritation of liquid compositions produced by methods of the invention.

Irritation at the treated site was reduced by an average of 22% after 2 hours, 39% after 4 hours and 55% after 24 hours. The corresponding figures for the untreated site were 11% after 2 hours, 17% after 4 hours and 28% after 24 hours. This may be seen in FIG. 6, in which the squared line represents the average irritation at the control site and the diamond line represents the treated site. This demonstrates the efficacy of compositions produced in accordance the methods of the invention to reduce skin irritation.

Trial 2: Prevention of UV-Induced Erythema

In order to study and evaluate the effectiveness of liquid compositions produced in accordance the methods of the invention to prevent erythema caused by UV light, five subjects between the ages of 23 and 55 were inducted into this study. The panel consisted of fair-skin individuals with skin types I, II and III, as defined by the Federal Register Vol. 64, No. 98:27690, 1999). Subjects were instructed to abstain from using any lightening and sunscreen product and refrain from sunbathing or tanning bed use for a period of at least 7 days prior to study commencement. The infrascapular area of the back to the right and left side of the midline was used. Within this area one 30 $cm^2$ (10 cm by 3 cm) rectangular test site and seven 9 $cm^2$ (3 cm by 3 cm) test sites were delineated with a gentian violet surgical skin marker. Test site 1 was treated with a liquid composition produced in accordance with the methods of the invention prior to UV exposure. The light source used was a Xenon Arc Solar Simulator with a continuous emission spectrum in the DVB range of 290 to 320 nm. The UV spectra produced are substantially equivalent to that of natural sunlight. UV exposure of 1.0-1.5 MED was applied to test site 1. Test site 5 was used as a control and not treated with a liquid composition produced in accordance with the methods of the invention prior to exposure to UV light of 1.0-1.5 MED. Delayed erythematic responses were recorded for each of the test sites at 24 hours post exposure and then approximately every 24 hours until dispensation of the erythema (return of homeostasis). Visual grading was conducted by a trained technician using a scale of 0 (no erythema) to 5 (erythema and edema in vesicles). Lab scale photographs were taken at baseline and again after 72 hours after initial application.

UV-induced erythema at test site 1 (pre-treated with a liquid composition produced in accordance with the methods of the invention) was reduced by 44% after 24 hours and 72% after 48 hours. The corresponding figures for the untreated site 5 were 0% after 24 hours and 20% after 48 hours. This demonstrates that liquid compositions produced in accordance with the methods of the invention are effective in preventing UV induced erythema.

Trial 3: Reduction of UV-Induced Erythema

In order to study and evaluate the effectiveness of liquid compositions produced in accordance with the methods of the invention to reduce erythema caused by UV light, five subjects between the ages of 23 and 55 were inducted into this study. The panel consisted of fair-skin individuals with skin types I, II and III, as defined by the Federal Register Vol. 64, No. 98:27690, 1999). Subjects were instructed to abstain from using of any lightening and sunscreen product and refrain from sunbathing or tanning bed use for a period of at least 7 days prior to study commencement. The infrascapular area of the back to the right and left side of the midline was used. Within this area one 30 $cm^2$ (10 cm by 3 cm) rectangular test site and seven 9 $cm^2$ (3 cm by 3 cm) test sites were delineated with a gentian violet surgical skin marker. Test site 3 was subjected to UV exposure using light from a Xenon Arc Solar Simulator with a continuous emission spectrum in the DVB range of 290 to 320 nm. The UV spectra produced are substantially equivalent to that of natural sunlight. UV exposure of 1.0-1.5 MED was applied to both test sites 3 and 5. Test site 5 was used as a control and not treated with a liquid composition produced in accordance with the methods of the invention after exposure to UV light of 1.0-1.5 MED. Test site 7 was neither treated with a liquid composition produced in accordance with the methods of the invention nor subjected to UV exposure. Delayed erythematic responses were recorded for each of the test sites at 24 hours post exposure and then approximately every 24 hours until dispensation of the erythema (return of homoestasis). Visual grading was conducted by a trained technician using a scale of 0 (no erythema) to 5 (erythema and edema in vesicles). Lab scale photographs were taken at baseline and again after 72 hours after initial application.

UV-induced erythema at test site 3 (treated with a liquid composition produced in accordance with the methods of the invention after UV exposure) was reduced by 30% after 24 hours and 50% after 48 hours. The corresponding figures for the untreated site 5 were 0% after 24 hours and 20% after 48 hours. No erythema was recorded at site 7. This confirms that liquid compositions produced in accordance with the methods of the invention are effective in reducing UV-induced erythema.

Trial 4: Strengthening of Hair

In order to study and evaluate the effectiveness of liquid compositions produced in accordance with the methods of the invention to strengthen hair, three female subjects between the ages of 23 and 30 were inducted into this study. In order to pre-condition the hair and keep the topical treatment consistent, the subjects were required to use a control shampoo for a period of 7 days prior to commencement and use only the control shampoo and test product for the study duration. The test product consisted of a leave-in conditioning serum containing 5% of a liquid composition produced in accordance with the methods of the invention as the only active ingredient. On the initial day of the study, each panellist arrived to the test facility with their head washed. The trained technician removed 10 hairs from the head of each of the panellist (2 hairs from each of the following test sites: right front, right back, left front, left back, centre). During the removal process the trained technician selected hair of similar length. Each hair was removed from the scalp via a cosmetic pincette, by grabbing one hair at a time, as close to the scalp as possible and rapid pulling. Each hair was separately evaluated for tensile strength using a Dia-Stron Rheometer. All subjects were instructed to use the test product once a day for five consecutive days. On the fifth day of the study, panellists were asked to apply the test product in the morning and return to the lab for final evaluation. The trained technician removed 10 hairs from the head of each of the panellist for tensile strength analysis. The source data are Dia-Stron Rheometer readings collected prior to initial application and again after 5 days of use. The data used in the statistical analysis reflect changes from baseline.

Figure 7:
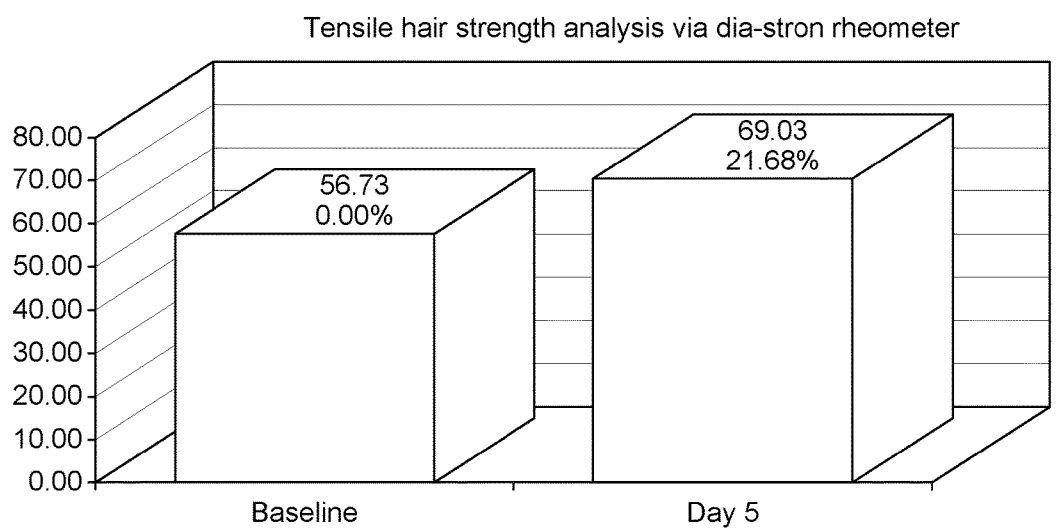
FIG. 7 shows the results of a clinical trial to determine the effectiveness in strengthening hair of liquid compositions produced by methods of the invention.

The readings collected at the conclusion of the study showed an improvement in tensile hair strength of 21.68% compared to the readings taken at the start of the study before the test material had been applied. These results can be seen in FIG. 7. This demonstrates that liquid compositions produced in accordance with the methods of the invention are effective in strengthening hair.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method of processing a mixture comprising at least two polysaccharides, and no more than 5% w/w of oil, and no more than 1% w/w of protein, wherein one of the polysaccharides is β-glucan, and wherein at least one polysaccharide is not β-glucan, wherein said method comprises:
   subjecting said mixture to at least one enzymatic treatment, said enzymatic treatment degrading at least a portion of at least one polysaccharide which is not β-glucan; and
   filtering the enzymatically treated mixture to obtain a mixture comprising beta-glucan.

2. The method of claim 1, wherein said mixture comprises no more than 1% w/w of oil.

3. The method of claim 1, wherein said filtering comprises filtering with a membrane filter.

4. The method of claim 1, wherein prior to enzymatic treatment and filtration, the β-glucan is present in said mixture at an amount of about 1.5% w/w.

5. The method of claim 1, wherein said method comprises at least two enzymatic treatments.

6. The method of claim 5, wherein at least one of said enzymatic treatments comprises treatment with an enzyme which degrades β-glucan, wherein the enzyme which degrades β-glucan is added for a pre-determined period of time before quenching the enzymatic reaction.

7. The method of claim 1, wherein said enzymatic treatment comprises treatment with amyloglucosidase.

8. The method of claim 1, wherein during said enzymatic treatment, said mixture is subjected to a high sheer force.

9. The method of claim 8, wherein said mixture is subjected to said high sheer force at a temperature of between 95° C. and 109° C.

10. The method of claim 1, wherein, prior to said enzymatic treatment, said mixture is heated to 135° C.

11. The method of claim 9, wherein said mixture has a pH which is reduced to between about 1.4 and 2.0.

12. The method of claim 9, wherein said mixture is allowed to cool naturally prior to said enzymatic treatment.

13. The method of claim 1, wherein at least one enzymatic treatment step comprises heating said mixture, and wherein said mixture is subsequently allowed to cool naturally.

14. The method of claim 1, wherein following said at least one enzymatic treatment, and prior to said filtration, said mixture is allowed to stand for at least two weeks.

15. The method of claim 14, wherein following said at least one enzymatic treatment, and prior to said filtration, said mixture is allowed to stand for at least five weeks.

16. The method of claim 1, wherein at least one polysaccharide which is not β-glucan is degraded to 6 DP.

17. The method of claim 1, wherein at least one polysaccharide which is not β-glucan is degraded to 4 DP.

18. The method of claim 1, wherein said at least one polysaccharide which is not (β-glucan is degraded to 1 DP.

19. The method of claim 1, wherein after filtration the filtrate is diluted or concentrated so as to provide a mixture with a concentration of (β-glucan of 2% w/w.

20. The method of claim 1, wherein after filtration the filtrate is diluted or concentrated so as to provide a mixture with a concentration of (β-glucan of 1% w/w.

\* \* \* \* \*